United States Patent
De Haan et al.

(10) Patent No.: US 9,924,896 B2
(45) Date of Patent: Mar. 27, 2018

(54) DEVICE, SYSTEM AND METHOD FOR DETERMINING THE CONCENTRATION OF A SUBSTANCE IN THE BLOOD OF A SUBJECT

(71) Applicant: KONINKLIJKE PHILIPS N.V., Eindhoven (NL)

(72) Inventors: Gerard De Haan, Helmond (NL); Mukul Rocque, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 272 days.

(21) Appl. No.: 14/736,319

(22) Filed: Jun. 11, 2015

(65) Prior Publication Data

US 2015/0366492 A1 Dec. 24, 2015

Related U.S. Application Data

(60) Provisional application No. 62/015,568, filed on Jun. 23, 2014.

(30) Foreign Application Priority Data

Jun. 23, 2014 (EP) .................................... 14173449

(51) Int. Cl.
*A61B 5/1455* (2006.01)
*A61B 5/00* (2006.01)

(52) U.S. Cl.
CPC ........ *A61B 5/14551* (2013.01); *A61B 5/1455* (2013.01); *A61B 5/7214* (2013.01)

(58) Field of Classification Search
None
See application file for complete search history.

(56) References Cited

U.S. PATENT DOCUMENTS

| 4,714,341 A | 12/1987 | Hamaguri et al. |
| 6,775,565 B1 | 8/2004 | Wieringa |

(Continued)

FOREIGN PATENT DOCUMENTS

| WO | 9749330 A1 | 12/1997 |
| WO | 0115597 A1 | 3/2001 |
| WO | 2013038288 A1 | 3/2013 |

OTHER PUBLICATIONS

Verkruysse, W., et al.; Remote plethysmographic imaging using ambient light; 2008; Optical Express; 16(26) 21434-21445.

(Continued)

*Primary Examiner* — Eric Winakur
*Assistant Examiner* — Marjan Fardanesh

(57) ABSTRACT

A device for determining the concentration of a substance in the blood of a subject, such as the oxygen saturation, which device reduces or removes the influence of specular reflection and/or subject motion, comprises an input unit for receiving detection signals reflected back or transmitted through a skin area of the subject in response to irradiation of the skin area by a radiation signal, a signal extraction unit for extracting at least three photo-plethysmography, PPG, signals at different wavelengths from said detection signals, a processing unit for normalizing said at least three PPG signals and forming a first difference signal between a first normalized PPG signal and a second normalized PPG signal and a second difference signal between a third normalized PPG signal and one other of the at least three normalized PPG signals and for forming a ratio between said first difference signal and said second difference signal, and an concentration detection unit for calculating the concentration of a substance in the blood of the subject based on said ratio.

20 Claims, 6 Drawing Sheets

(56) References Cited

U.S. PATENT DOCUMENTS

| | | |
|---|---|---|
| 7,738,935 B1 | 6/2010 | Turcott |
| 2004/0024297 A1 | 2/2004 | Chen et al. |
| 2007/0219439 A1 | 9/2007 | Vilser et al. |
| 2009/0082642 A1 | 3/2009 | Fine |
| 2013/0215244 A1 | 8/2013 | Mestha et al. |
| 2014/0221728 A1 | 8/2014 | Bodlaender et al. |

OTHER PUBLICATIONS

Wieringa, F. P., et al.; Contactless Multiple Wavelength Photoplethysmographic Imaging: A First Step Toward "SpO2 Camera" Technology; 2005; Annals of Biomedical Engineering; 33(8)1034-1041.

DEVICE, SYSTEM AND METHOD FOR DETERMINING THE CONCENTRATION OF A SUBSTANCE IN THE BLOOD OF A SUBJECT

CROSS REFERENCE TO RELATED APPLICATIONS

This application claims the benefit of U.S. provisional application Ser. No. 62/015,568 filed Jun. 23, 2014 and EP application 14173449.1 filed Jun. 23, 2014, both of which are incorporated herein by reference.

FIELD OF THE INVENTION

The present invention relates to a device, system and method for determining the concentration of a substance, such as the concentration of oxygen (oxygen saturation, SpO2), bilirubin, CO2, etc., in the blood of a subject, such as a person or animal.

BACKGROUND OF THE INVENTION

Vital signs of a person, for example the heart rate (HR), the respiration rate (RR) or the arterial blood oxygen saturation (SpO2), serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmittance and/or reflectivity at different wavelengths (typically red and infrared), the blood oxygen saturation can be determined.

Conventional pulse oximeters (also called contact PPG device herein) for measuring the heart rate and the (arterial) blood oxygen saturation (also called SpO2) of a subject are attached to the skin of the subject, for instance to a fingertip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmittance of the same area or volume of tissue at two different wavelengths. This is referred to as time-division-multiplexing. The transmittance over time at each wavelength gives the PPG waveforms for red and infrared wavelengths. Although contact PPG is regarded as a basically non-invasive technique, contact PPG measurement is often experienced as being unpleasant and obtrusive, since the pulse oximeter is directly attached to the subject and any cables limit the freedom to move and might hinder a workflow.

Fast and reliable detection and analysis of a pulse signal and oxygen saturation level (SpO2) is one of the most important activities in many healthcare applications, which becomes crucial if a patient is in a critical condition. In those situations, pulsatility of a heart beat signal is very weak, and therefore, the measurement is vulnerable to any sort of artifacts.

Modern photoplethysmography sensors do not always provide fast and reliable measurement in critical situations. For instance, contact finger pulse oximeters (based on transmissive PPG) are vulnerable to motion of a hand, and fails in case of centralization of a patient due to lower blood volumes on body peripherals. Contact forehead pulse oximeter sensors (using a reflective PPG measurement mode) are supposed to be more robust to a centralization effect. However, the accuracy, robustness and responsiveness of a forehead sensor depends heavily on correct positioning of a sensor on a forehead and proper pressure applied to a skin (too tight application of a sensor might reduce a local blood pulsatility, too loose application might lead to non-reliable measurements due to motion artifacts and/or venous pulsatility).

Recently, non-contact, remote PPG (rPPG) devices (also called camera rPPG devices) for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications. This technology particularly has distinct advantages for patients with extreme skin sensitivity requiring vital signs monitoring such as NICU patients with extremely fragile skin or premature babies.

Verkruysse et al., "Remote plethysmographic imaging using ambient light", Optics Express, 16(26), 22 Dec. 2008, pp. 21434-21445 demonstrates that photoplethysmographic signals can be measured remotely using ambient light and a conventional consumer level video camera, using red, green and blue color channels.

Wieringa, et al., "Contactless Multiple Wavelength Photoplethysmographic Imaging: A First Step Toward "SpO2 Camera" Technology," Ann. Biomed. Eng. 33, 1034-1041 (2005), discloses a remote PPG system for contactless imaging of arterial oxygen saturation in tissue based upon the measurement of plethysmographic signals at different wavelengths. The system comprises a monochrome CMOS-camera and a light source with LEDs of three different wavelengths. The camera sequentially acquires three movies of the subject at the three different wavelengths. The pulse rate can be determined from a movie at a single wavelength, whereas at least two movies at different wavelengths are required for determining the oxygen saturation. The measurements are performed in a darkroom, using only one wavelength at a time.

Specular reflectance of light from the skin's surface causes calibration errors leading to incorrect measurement of the concentration of various substances, such as SpO2, CO2, bilirubin, etc. in the subject's blood. Current ideas necessitate the use of polarizers in the measurement setup which are difficult to align and prove to make for a difficult setup in practice.

Further, subject motion causes an incorrect measurement of such a substance, such as SpO2, as conventionally determined. Consequently, recently proposed remote SpO2 measurement requires very stationary subjects, while contact SpO2 sensors conventionally use accelerometers to compensate for motion artifacts.

WO 01/15597 A1 discloses an imaging apparatus for representing an image of concentration ratios between a first and a second substance in a region of interest of an object, with different measuring values being represented with different colors and/or gray shades. The apparatus comprises a light source capable of irradiating the object with light, which light comprises at least three wavelengths $\lambda_1$, $\lambda_2$ and $\lambda_3$, $\lambda_3$ being an isobestic wavelength, $\lambda_1$ being a wavelength at which the first substance has a lower absorption than the second substance, and $\lambda_2$ being a wavelength at which the first substance has a higher absorption than the second substance. The apparatus further comprises detection means comprising a matrix of pixel detectors, for representing a virtually instantaneous image of the region of interest.

U.S. Pat. No. 7,738,935 B1 discloses methods and devices for reduction of motion-induced noise in pulse oximetry when measuring blood oxygen saturation. A portion of the light having the first wavelength, a portion of light having the second wavelength and a portion of the light having the third wavelength are received. A first signal is produced based on the received portion of light having the first wavelength. Similarly, a second signal is produced based on the received portion of light having the second wavelength, and a third signal is produced based on the received portion of light having the third wavelength. A difference between the second signal and the first signal is determined, wherein the difference signal is first plethysmography signal. Similarly, a difference is determined between the third signal and the first signal to produce a second plethysmography signal. Blood oxygen saturation is then estimated using the first and second plethysmography signals.

SUMMARY OF THE INVENTION

It is an object of the present invention to provide a device, system and method for determining the concentration of a substance in the blood of a subject that remove or at least reduce the influence of specular reflectance and/or motion artifacts.

In a first aspect of the present invention a device for determining the concentration of a substance in the blood of a subject is presented comprising
  an input unit configured to receive detection signals reflected back or transmitted through a skin area of the subject in response to irradiation of the skin area by a radiation signal,
  a signal extraction unit configured to extract at least three photo-plethysmography, PPG, signals at different wavelengths from said detection signals,
  a processing unit configured to normalize said at least three PPG signals and to form a first difference signal between a first normalized PPG signal and a second normalized PPG signal and a second difference signal between a third normalized PPG signal and one other of the at least three normalized PPG signals and to form a ratio between said first difference signal and said second difference signal, and
  a concentration detection unit configured to calculate the concentration of a substance in the blood of the subject based on said ratio.

In a further aspect of the present invention a corresponding method is presented.

In a still further aspect of the present invention a system for determining the concentration of a substance in the blood of a subject is presented comprising
  a radiation detection unit for detecting detection signals reflected back or transmitted through a skin area of the subject in response to irradiation of the skin area by a radiation signal, and
  a device as disclosed herein for determining the concentration of a substance in the blood of the subject from said detection signals.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed methods, processor, computer program and medium have similar and/or identical preferred embodiments as the claimed device and as defined in the dependent claims.

The present invention is based on the idea to use an additional wavelength channel compared to known devices and methods for determining the concentration of a substance like SpO2, which use two wavelength channels. From these at least three wavelength channels difference signals are computed, from which a ratio-of ratio is computed. This can completely remove the effect of specular reflectance and lead to a situation where the use of polarizers, as conventionally used for correct calibration, is no longer necessary. Alternatively or additionally, using the third wavelength channel, the influence of motion can be eliminated from the ratio-of ratios. A greatly enhanced motion robustness is obtained, while the technology can be used for both contact and remote SpO2 measurement systems.

For reducing the influence of motion said processing unit is configured to normalize said PPG signals, in particular by (individually) dividing the PPG signals by their respective temporal means (DC), before forming said difference signals.

In an embodiment said signal extraction unit is configured to extract two PPG signals at two wavelengths of infrared light the first and third PPG signals and one wavelength of visible or infrared light from said detection signals.

In particular for SpO2 detection, said signal extraction unit is preferably configured to extract a first PPG signal at a first wavelength in the range from 780 nm to 850 nm, a second PPG signal at a second wavelength in the range from 550 to 780 nm and a third PPG signal at a third wavelength in the range from 840 nm to 1000 nm. Practical examples are 810 nm for the first wavelength, a wavelength between 840 and 1000 nm as third wavelength and 650 nm (or, if it shall also be invisible, between 700 and 780 nm) as second wavelength. For other substances the same or other wavelengths may be appropriate, wherein preferably at least one wavelength is between 400 and 500 nm for bilirubin detection.

Preferably, the two PPG signals at two wavelengths of infrared light represent the first and third PPG signals and the PPG signal at the wavelength of visible or infrared light represents the second PPG signal, wherein said processing unit is preferably configured to form the first difference signal by subtracting the second normalized PPG signal from the first normalized PPG signal, to form the second difference signal by subtracting the first normalized PPG signal from the third normalized PPG signal and to form said ratio (i.e. the ratio-of-ratios) by dividing said first difference signal by said second difference signal. In this way the negative effects of specular reflection and/or motion can be reduced or even totally removed.

With three wavelengths it is preferred to have in the numerator the highest sensitivity to the substance (e.g. SpO2), i.e. to take the difference between 650 nm (the near visible wavelength) and the longest wavelength (between 840 and 1000 nm). In the denominator it is preferred to have a low sensitivity to the substance and a difference that never becomes zero. It should be noted, however, that the opposite also works fine, i.e. low sensitivity in the numerator and high sensitivity in the denominator. Sensitivity in both numerator and denominator may also be lead to acceptable results, particularly if they trend in opposite sense (increase in one while decrease in the other). The only case that may not work is when they have an equal sensitivity to the substance.

A good choice (with three wavelengths) is the difference between 800 and 840 to 1000 nm. A somewhat attractive choice for the denominator is to build a weighted sum of all three wavelengths with coefficients that sum up to zero, selected such that there is no sensitivity to the substance. For example, the following equation may be used for determining SpO2: (IR870−660)/(0.17*660+0.83*IR870−IR810), wherein "IR" means "infrared" and the number behind "IR" means the wavelength. The advantage is that SpO2 is now linearly related to the ratio. Generally, a linear relation is not required, since it is generally possible to correct for non-linearities.

In a particular implementation said concentration detection unit is configured to calculate the concentration of a substance in the blood by multiplying said ratio with a second calibration parameter and subtracting the result of said multiplication from a first calibration parameter. Said calibration parameters are generally constants, which are preferably obtained experimentally. An alternative is to use a look-up table to translate the ratio to the concentration of the substance. This is particularly recommended if the relation is non-linear.

As mentioned above said detection signals are either sensor signals of a contact PPG sensor contacting said skin area of the subject or images of at least said skin area of the subject obtained by an imaging unit, in particular a white-balanced imaging unit. The use of a white-balanced imaging unit, e.g. a white-balanced camera, provides that the influence of specular reflection can be removed or reduced. Generally, white-balancing is only required in case the PPG signals are not normalized before forming the difference signals, as proposed in another embodiment.

Accordingly, in the proposed system said radiation detection unit preferably either comprises a contact PPG sensor configured to contact said skin area of the subject for detecting sensor signals as detection signals or comprises an imaging unit, in particular a white-balanced imaging unit, for obtaining images of at least said skin area of the subject as detection signals.

In another aspect a device for determining the oxygen saturation of a subject is presented comprising:
- an input unit configured to receive detection signals reflected back or transmitted through a skin area of the subject in response to irradiation of the skin area by a radiation signal,
- a signal extraction unit configured to extract at least three photo-plethysmography, PPG, signals at different wavelengths from said detection signals,
- a processing unit configured to normalize said at least three PPG signals and to form a first difference signal between a first normalized PPG signal and a second normalized PPG signal and a second difference signal between a third normalized PPG signal and one other of the at least three normalized PPG signals and to form a ratio between said first difference signal and said second difference signal, and
- a oxygen saturation detection unit configured to calculate the oxygen saturation of the subject based on said ratio.

Preferably, said above processing units are configured to form the ratio between estimated AC amplitudes, in particular e.g. the standard deviation or a more robust amplitude estimate, of said first difference signal and said second difference signal. As explained above and as is clear from the fact that PPG signals are evaluated according to the present invention, the AC variations of the obtained PPG signals over time are evaluated (which occur when the volume of the blood in the skin is varying due to the beating of the heart) as the invention aims at estimating the oxygenation in the arterial blood only (which is pulsing). Particularly the ratio of the estimated AC amplitudes in the two difference signals is used, e.g. the ratio of the standard deviation (or a more robust amplitude estimate, like a median of peak-minus-valley-values, or yet another estimate) of the difference signals.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
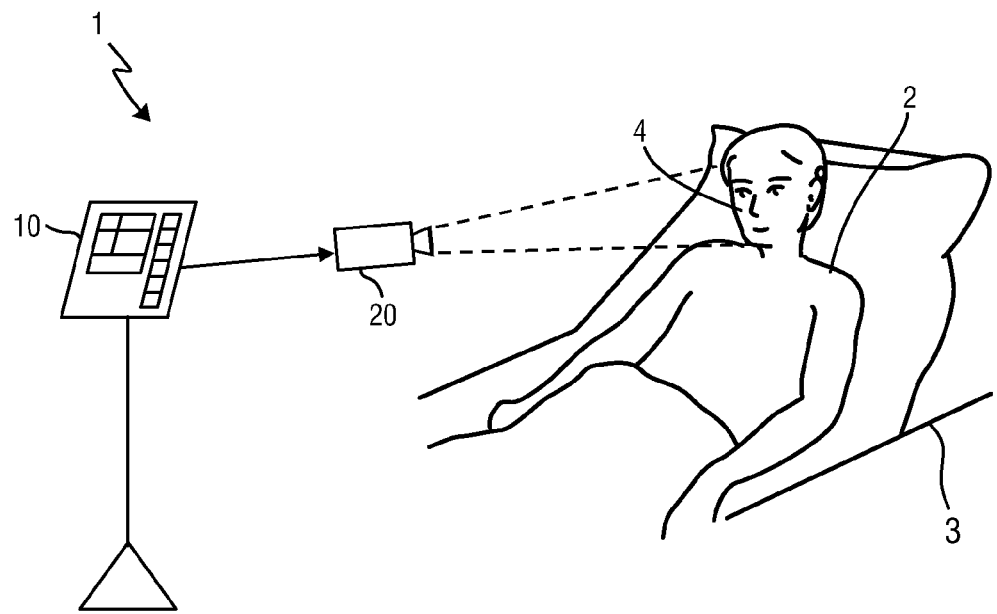
FIG. 1 shows a schematic diagram of a first embodiment of a system and device for determining the concentration of a substance in the blood of a subject.

FIG. 1 shows a schematic diagram of a first embodiment of a system 1 and device 10 for determining the concentration of a substance in the blood of a subject 2. Hereinafter, the invention shall be explained by determining the oxygen saturation (SpO2) in the subject's blood. However, all explanations mutually apply for determining the concentration of other substances in the subject's blood, such as CO2, bilirubin, etc. Other substances may require the use of different wavelengths though. The subject 2 in this example is a patient lying in a bed 3, e.g. in a hospital or other healthcare facility, but may also be a neonate or premature infant, e.g. lying in an incubator, or person at home or in a different environment. Besides the device 10 the system 1 generally comprises a radiation detection unit for detecting detection signals reflected back or transmitted through a skin area 4 of the subject 2 in response to irradiation of the skin area 4 by a radiation signal.

In this example the radiation detection unit is an imaging unit 20, in particular a camera (also referred to as detection unit or as camera-based or remote PPG sensor), for obtaining images of at least said skin area 4 of the subject 2 as detection signals. The skin area 4 is preferably an area of the face, such as the cheeks or the forehead, but may also be another area of the body, such as the hands or the arms. The radiation signal in this example is the ambient light, e.g. as provided by the sun and/or from room lighting. In other embodiment special light source(s) are provided for illuminating the subject 2 or at least the skin area 4 of the subject 2 with radiation of particular wavelength(s) and/or (only) at times of measurement (e.g. during night time).

The image frames captured by the camera may particularly correspond to a video sequence captured by means of an analog or digital photosensor, e.g. in a (digital) camera. Such a camera usually includes a photosensor, such as a CMOS or CCD sensor, which may also operate in a specific spectral range (visible, IR) or provide information for different spectral ranges. The camera may provide an analog or digital signal. The image frames include a plurality of image pixels having associated pixel values. Particularly, the image frames include pixels representing light intensity values captured with different photosensitive elements of a photosensor. These photosensitive elements may be sensitive in a specific spectral range (i.e. representing a specific color). The image frames include at least some image pixels being representative of a skin portion of the subject. Thereby, an image pixel may correspond to one photosensitive element of a photo-detector and its (analog or digital) output or may be determined based on a combination (e.g. through binning) of a plurality of the photosensitive elements.

PPG systems, SpO2 is computed by measuring this PPG amplitude (caused by pulsatile blood in arteries) at two distinct wavelengths. The ratio between the PPG amplitudes (DC normalized) of the two wavelengths gives the equation 1 for the computation of SpO2:

$$SpO_2 = C_1 - C_2 \frac{R}{IR}$$

with $$R = \frac{AC_{Red}}{DC_{Red}} \text{ and } IR = \frac{AC_{IR}}{DC_{IR}},$$

whereby $AC_{Red}$ may also be expressed as $\sigma(R)$ and represents an estimate of the amplitude of the signal R. The constants C1 and C2 in the equation above are called the calibration parameters (or calibration constants). Calibration refers to inter-person and intra-person calibration leading to incorrect SpO2 measurements and errors can be caused due to a number of factors. One of these causes has been found to be subject motion, which leads to motion-induced intensity variations in addition to the intensity variations due to PPG. Another one of these causes has been found to be specular reflectance, the mirror like reflectance of light of the skin surface, which makes camera SpO2 measurement different from contact sensor based measurement.

Figure 2:
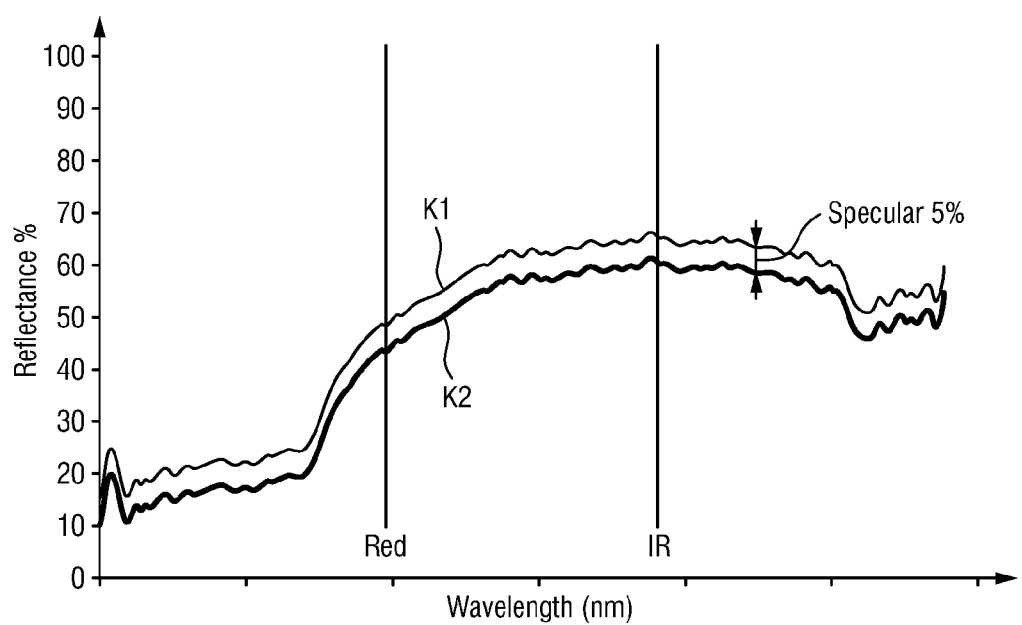
FIG. 2 shows a diagram illustrating the effect of specular reflectance.

Pulsatility only occurs in that fraction of the light that has penetrated into the skin and is diffusely reflected. The specularly reflected light reaching the camera 20 does not contain any light modulation due to arterial blood pulsatility and hence causes a decrease in relative pulsatility of the total reflected light. Consequently there will be errors in SpO2 measurement depending on the fraction of the specularly reflected light in the total reflected light from the skin. Specular reflectance depends on the angles between the camera, the subject and the illumination source and is an additive property adding an equal but unknown amount of DC reflectance across all wavelengths equally as shown in FIG. 2 depicting a curve K1 of the diffuse and specular reflectance and a curve K2 of the diffuse reflectance only, both curves over wavelengths of light.

The effect of specular reflectance can be shown with a simple computation as shown in the following table.

|  | DC Red | DC IR | AC Red Pulsatility = 0.1 | AC IR Pulsatility = 0.2 | RR ACred/DCred ACir/DCir | SpO2 C1 = 123; C2 = 54 |
| --- | --- | --- | --- | --- | --- | --- |
| Without Specular reflectance (Ideal condition) | 0.4 | 0.55 | 0.04 | 0.11 | 0.5 | 96 |
| With Specular reflectance (+5%) | 0.45 | 0.6 | 0.04 | 0.11 | 0.4846 | 96.82 |

The obtained detection signals, i.e. in this embodiment the sequence of images, are provided to the device 10 for further processing that will be explained below in more detail.

While such a system can generally be used for obtaining various vital signs by use of the known remote PPG technology, it is used according to the present invention for determining the oxygen saturation of arterial blood (also referred to as SpO2) within the subject 2. The light reflected back from the skin of the subject is modulated by the pulsatile arteries and the modulation amplitude contains the information of the blood saturation levels. In known remote Since the additive specular reflectance seen by the camera does not contain any modulated light the AC component for the wavelengths remains constant. This causes an overall change in the double ratio leading to a slightly different SpO2 and hence a different calibration constant. This effect gets magnified based on the relative difference between the reflectance for the two wavelengths. A higher reflectance, i.e. a higher value of the numerator (i.e. for the wavelength of red light) with respect to the denominator (i.e. for the wavelength of IR light), leads to a lower SpO2 (and hence a higher C1 to compensate) and vice versa.

One solution to reduce or remove this effect is the use of cross-polarization. The polarizers are attached at the illumination source and the cameras and oriented in such a way that all specularly reflected light is blocked away. Even though this is a generic solution, one key problem lies in the low practicality of this solution.

To start with unpolarized ambient light has to be eliminated from the scene. Furthermore, large illumination sources, as currently being used, require large polarization sheets of high quality. Further, such a large illumination source does not allow the polarization planes to be normal with respect to the camera-subject source geometry, a condition necessary for the removal of specular reflectance. This then necessitates the use of different illumination sources which might not be very practical.

Hence, the present invention uses an additional wavelength with which the effect of specular reflectance can be removed from the measurement of the SpO2. The specular reflection disappears in a difference channel built from two wavelengths, in particular if the camera 20 has been white-balanced, i.e. the light source gives equal signal in both channels corresponding to said wavelengths. Further, the conventionally used "red" and "infrared" channels are replaced by two "difference" channels eliminating the influence of specular reflection, while the SpO2 sensitivity remains, provided at least one of these difference channels exhibits a pulsatility that varies with the oxygenation level.

As a consequence of using two difference signals, three wavelengths are now used for this SpO2 measurement. The use of an additional wavelength channel removes the need of polarization filters for the removal of specular reflectance and greatly simplifies the setup. The white-balanced camera setup ensures that the specular reflection is equally strong in all wavelengths. Once this condition has been satisfied difference signals between the wavelengths remove any effect of specular reflectance (since specular reflectance is now equal across wavelengths in a white-balanced camera). The difference signals can then be used for computing an accurate SpO2, using the following equation:

$$SpO_2 = C_1 - C_2 \frac{IR - R}{IR2 - IR}$$

Figure 3:
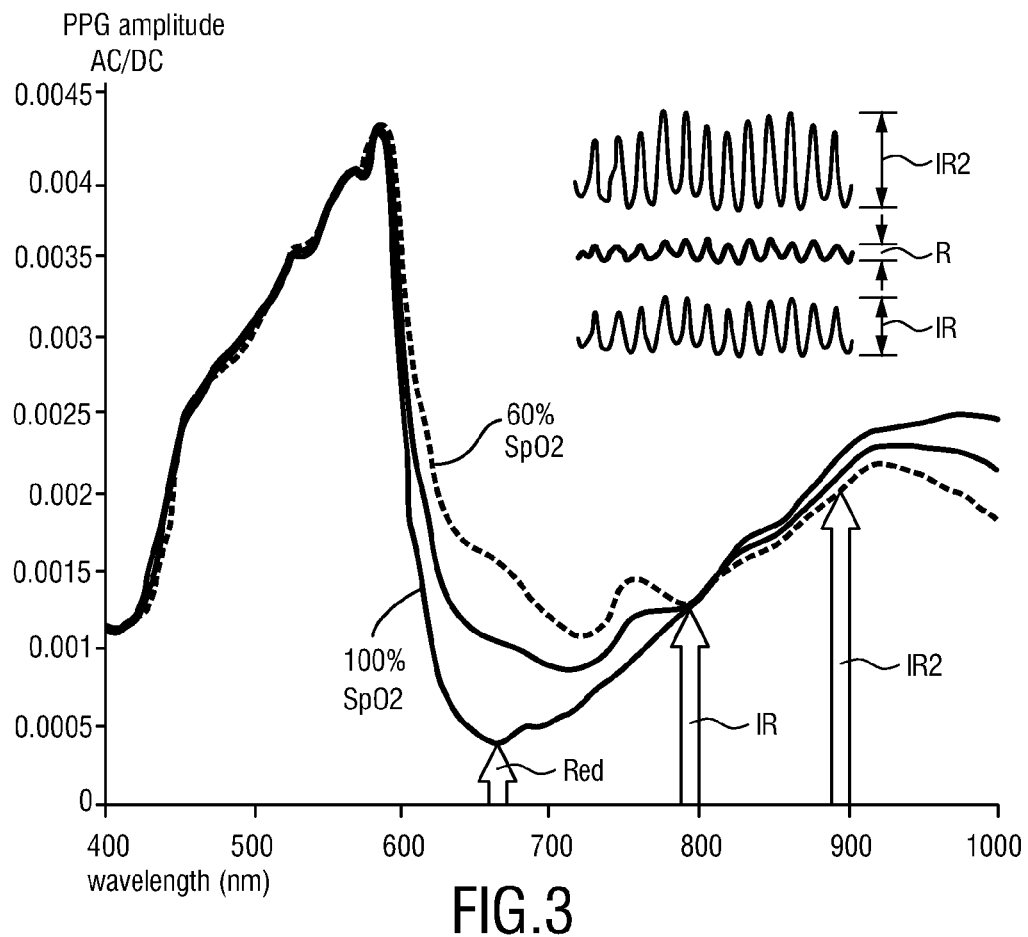
FIG. 3 shows a diagram of the PPG amplitude for various values of SpO2 over wavelength.

This calculation is then free from the miscalibration effects of specular reflectance as shown in FIG. 3. Generally, the calibration constants differ from the ones used in the conventional systems using two wavelengths. Said calibration constants are e.g. established experimentally or through simulation.

The above formula for computing SpO2 may also be expressed as $$SpO_2 = C_1 - C_2 \frac{\sigma(IR - R)}{\sigma(IR2 - IR)}$$

with R, IR, IR2 representing the average pixel intensity of the PPG signal in the corresponding wavelength range, wherein a PPG signal is preferably obtained from a region of interest in a sequence of images, and $\sigma(x)$ representing an estimate of the amplitude of the AC-component of x, which can be computed in different ways (in an embodiment $\sigma(x)$ represents the standard deviation of the time varying signal x).

The camera(s) is preferably white-balanced to ensure specular reflectance is completely removed in the difference signals. This may be obtained by firstly white-balancing the camera setup. Since the wavelengths might not necessarily be in the visible range a calibration surface capable of reflecting all wavelengths is preferably used. With this setup and a given illumination the cameras can be white-balanced according to the standard procedure and the DC levels of all the wavelengths equalized.

The white-balancing holds as long as the illumination has a constant spectral response. Changes in the illumination's spectral response would still be tolerable as long as it is constant across all wavelengths. However, if at any time the spectral response of the illumination changes non-uniformly across the wavelengths, a recalibration is preferably applied for the complete elimination of specular reflection. Without such re-calibration, still an incomplete compensation of the specular reflection would result.

Since the SpO2 measurement is now a measure of the ratio of the difference (normalized) PPG signals instead of the conventionally used single wavelength normalized PPG signals, the calibration constants C1 and C2 changes. The computations for these constants would follow the white-balance calibration and be the same as for the conventional SpO2 measurements done with a camera.

With all calibrations done SpO2 can now be correctly measured without the effect of specular reflectance by correctly estimating the difference signals.

PPG-induced pulsatility is much smaller in the normalized red channel than in the normalized infrared channel for healthy SpO2 levels, although the levels can become close to each other for very low SpO2 values. Motion induced intensity variations however, are typically of equal strength in both channels and consequently lead to an under-estimation of the actual SpO2 estimates.

In conventional contact PPG sensors a similar problem may occur, and sometimes accelerometers are included in the device to compensate for motion artifacts. Clearly, in a camera-based PPG system such solution is infeasible.

In the above it has been shown that the specular reflection disappears in a difference channel built from two non-normalized wavelength-signals, assuming the use of a single light-source for the entire light spectrum and a single camera with multi-wavelength sensitivity. Replacing the conventionally used "normalized red" and "normalized infrared" channels by two channels each resulting as the difference between two normalized channels representing a particular wavelength (interval) eliminates the influence of motion, since this is identical in the individual normalized channels. In this case, the SpO2 sensitivity remains, provided at least one of these difference channels exhibits a pulsatility that varies with the oxygenation level. The difference signals can then be used for computing an accurate SpO2, using the following equation:

$$SpO_2 = C_1 - C_2 \frac{IR_n - R_n}{IR2_n - IR_n}$$

Here, the index "n" indicates the DC normalization of the respective PPG signal. As a consequence of using two difference signals, three wavelengths are used for this SPO2 measurement system. The calibration constants differ from the ones used in the conventional system and in the above described embodiment of the present invention and are e.g. established experimentally or through simulation.

The above formula for computing SpO2 may also be expressed as $$SpO_2 = C_1 - C_2 \frac{\sigma(IR/DC_{IR} - R/DC_R)}{\sigma(IR2/DC_{IR2} - IR/DC_{IR})}$$

with $R_n = R/DC_R$, $IR_n = IR/DC_{IR}$, $IR2_n = IR2/DC_{IR2}$ representing the individually normalized signals for the corresponding wavelength range.

In a preferred embodiment a first PPG signal (IR) is extracted at a first wavelength in the range from 780 nm to 850 nm, a second PPG signal (R) is extracted at a second wavelength in the range from 550 to 780 nm and a third PPG signal (IR2) is extracted third wavelength in the range from 850 nm to 1000 nm. An example choice valid for SpO2 uses 660 nm, 810 nm and 870 nm.

Figure 4:
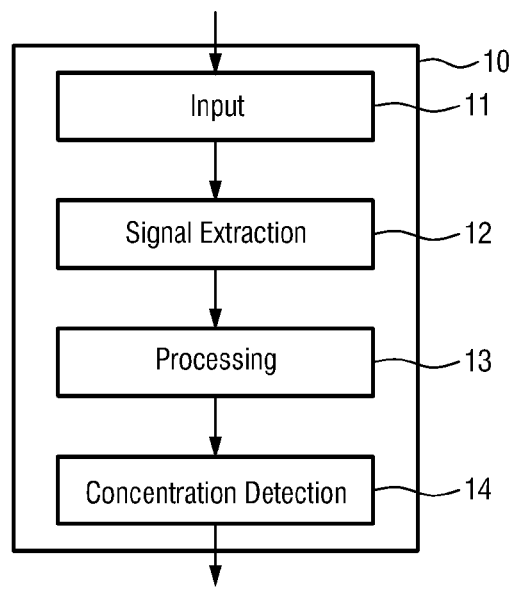
FIG. 4 shows a schematic diagram of a device according to the present invention.

A schematic diagram of a device 10 for determining the oxygen saturation of the subject 2 is depicted in FIG. 4. The device 10 comprises an input unit 11 for receiving detection signals reflected back or transmitted through a skin area of the subject in response to irradiation of the skin area by a radiation signal. The detection signals may e.g. be obtained by the imaging unit 20 or a contact PPG sensor as explained below in another embodiment of the system. A signal extraction unit 12 extracts at least three photo-plethysmography (PPG) signals at different wavelengths from said detection signals. A processing unit 13 forms a first difference signal between a first PPG signal and a second PPG signal and a second difference signal between a third PPG signal and the first PPG signal. Further, the processing unit 13 forms a ratio between said first difference signal and said second difference signal. Based on said ratio an oxygen saturation detection unit 14 calculates the oxygen saturation of the subject.

A simulation and an actual measurement have been performed from a video sequence of a subject. Over time, the pulse signal amplitude in the red channel increases whereas the pulse signal in IR and IR2 channels stays the same, simulating a decreasing SpO2. All the signals further suffer from simulated motion (identical in all channels) and noise of similar strength but independent in all channels.

Figure 5A:
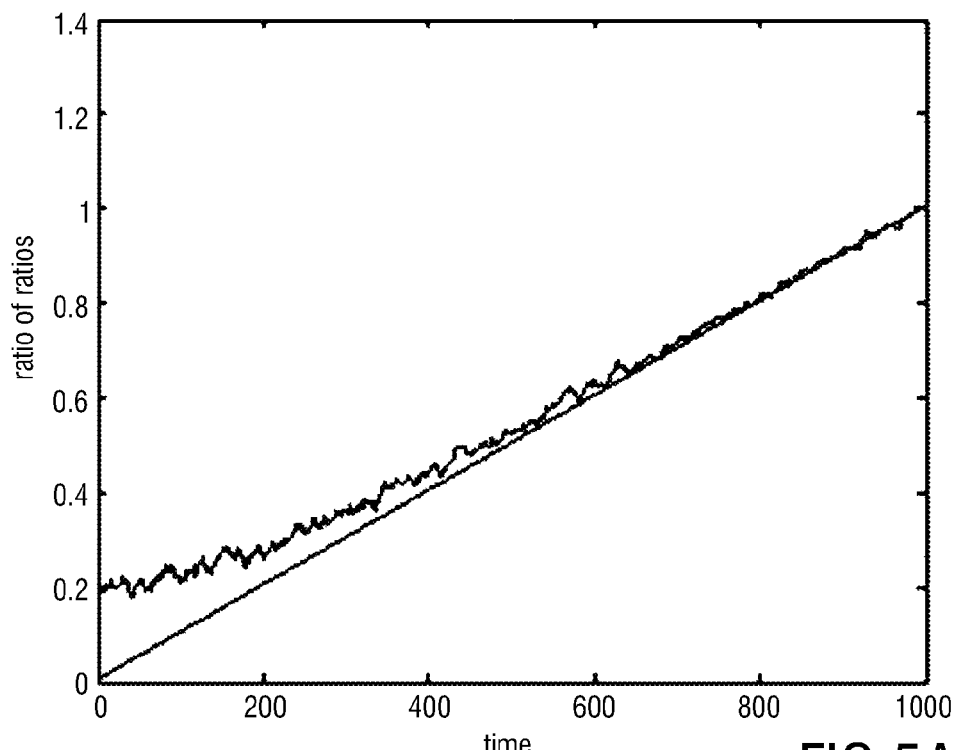
FIG. 5a shows simulation results of SpO2 measurement in a simulation with two wavelengths in a static subject.
Figure 5B:
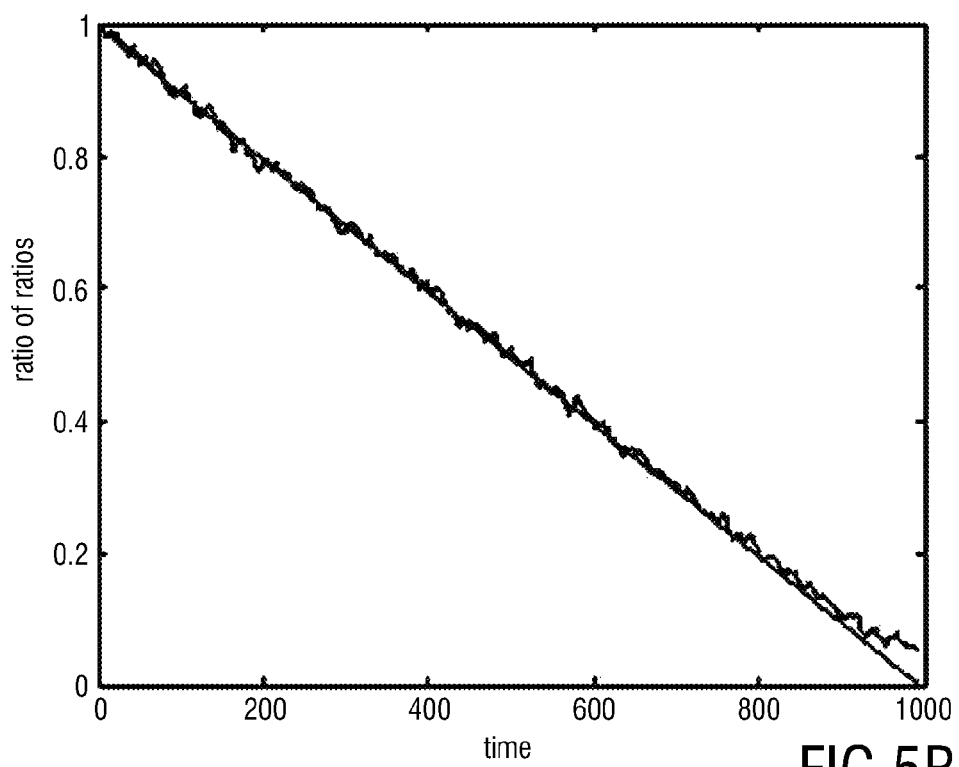
FIG. 5b shows simulation results of SpO2 measurement in a simulation with three wavelengths in a static subject.

Based on this simulation model, the ratio-of-ratios has been computed, i.e. the basis for SpO2 estimation without the calibration, for the conventional SpO2 measurement with two wavelengths and the proposed motion-robust SpO2 measurement with three wavelengths. FIG. 5, shows the simulation results along with the ideal curves obtained in the absence of noise and motion, wherein FIG. 5A shows the result when using two wavelengths and FIG. 5B shows the result when using three wavelengths. These curves are different, reflected by the different angle of the lines, indicating a different calibration. The three wavelengths system is not affected by motion. The straight lines in both figures give the ideal ratio-of-ratios, i.e. without noise and motion.

Figure 6A:
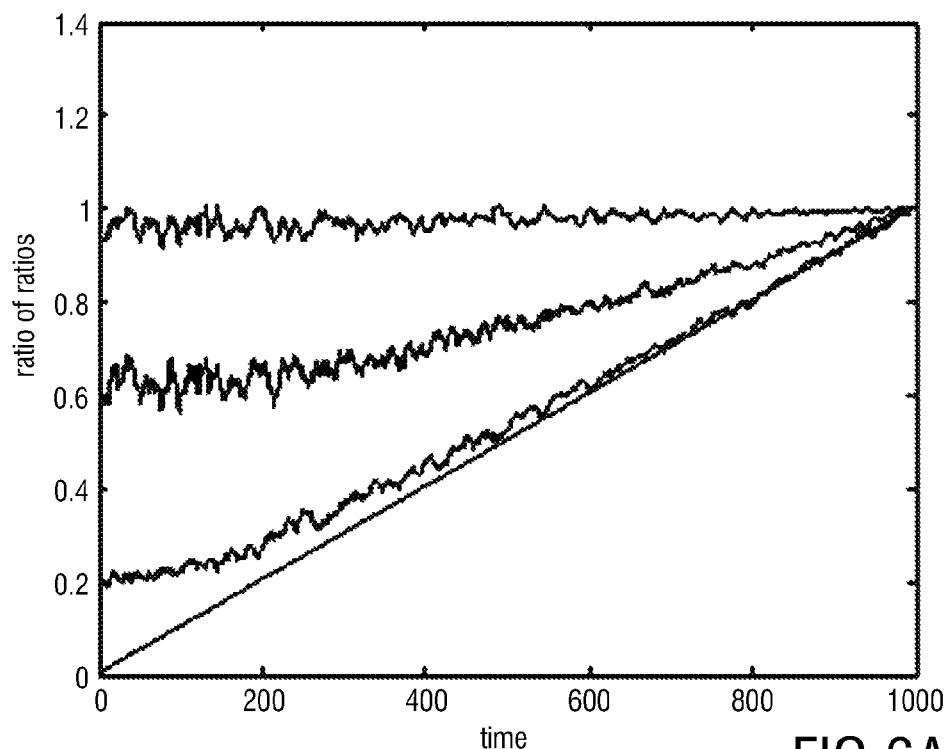
FIG. 6a shows simulation results of SpO2 measurement in a simulation with two wavelengths with varying amounts of simulated motion.
Figure 6B:
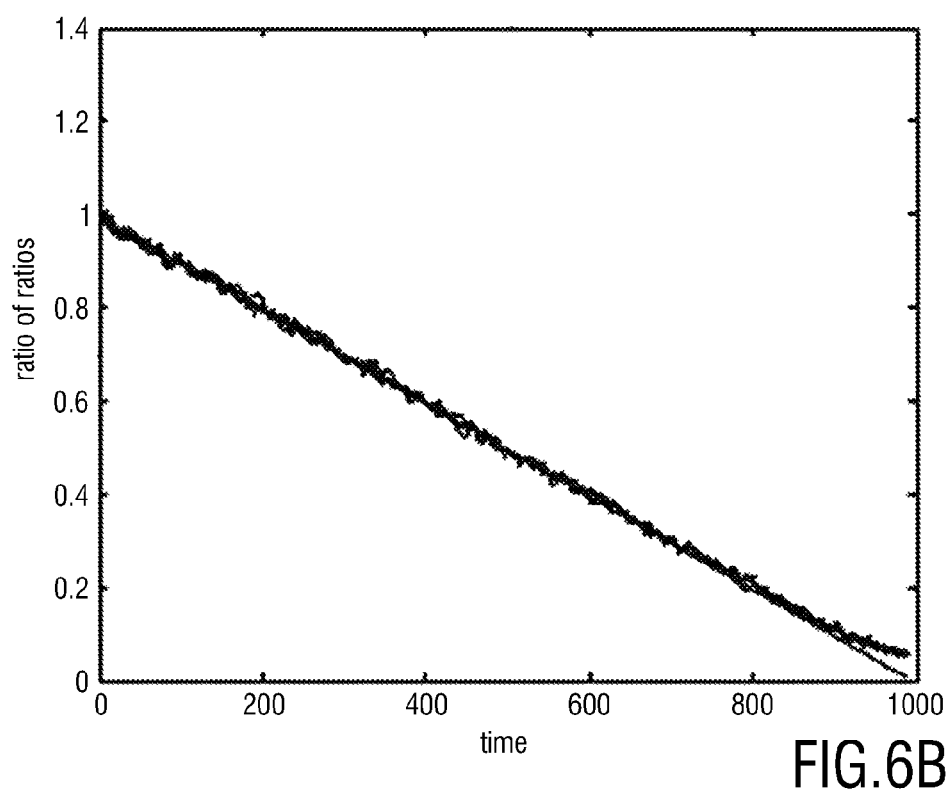
FIG. 6b shows simulation results of SpO2 measurement in a simulation with three wavelengths with varying amounts of simulated motion.

The deviation between the ideal and the noise-containing curves show the amount of error that can be expected in the final SpO2 computation. This deviation depends on the amount of motion present and becomes worse with an increasing amplitude of motion with respect to the pulsatile signal as shown in FIG. 6. FIG. 6 shows simulation results of SpO2 measurement with two wavelengths (FIG. 6A) and three wavelengths (FIG. 6B) with varying amounts of simulated motion. Each curve indicates the magnitude of motion w.r.t the maximum signal in the red channel added.

In a second set of experiments the intensity variations were measured in an actual SpO2 camera system with three wavelengths. Due to practical limitations, red, infrared and green were used in this setup and the channels were registered with separate cameras.

Figure 7:
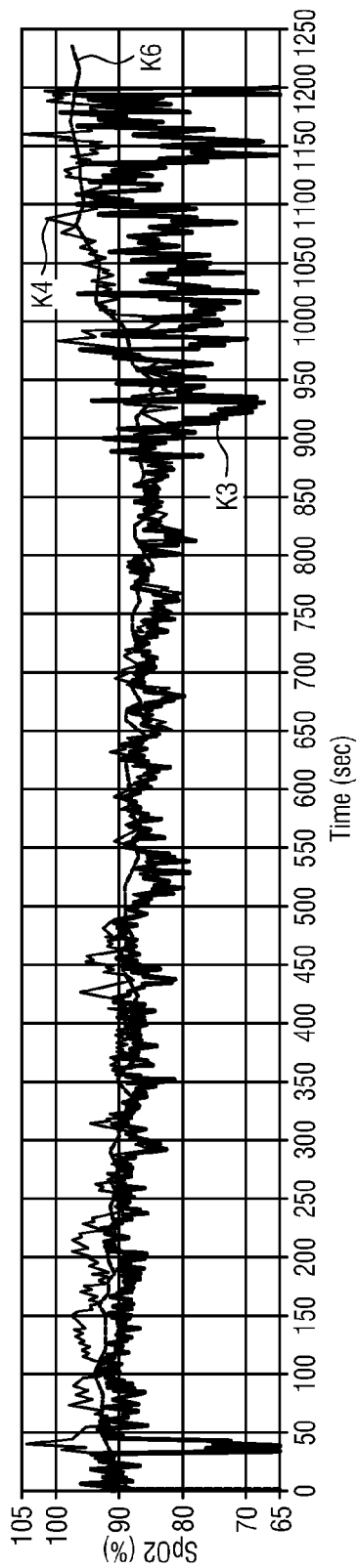
FIG. 7 shows simulation results of SpO2 measurement in a second simulation with different systems in a static subject.

The first of these experiments was done using an almost completely static subject, with an experiment meant to induce SpO2 variations. This experiment would also help in determining the C1, C2 constants for the three channel difference measurement. In this experiment the subject was initially subjected to a low oxygen (~15%) saturated environment (0 to 900 sec) before being subjected to normal oxygen (~21%) levels (900 sec+). As can be seen from FIG. 7, even during such very static situations the conventional two channel measurement method is significantly affected. This is due to the fact that at higher SpO2 levels the PPG amplitude for the red channel becomes very small and consequently is more susceptible to the noise due to (micro-amplitude) motion. Curve K3 shows the SpO2 measurement with three channel difference signals, Curve K4 shows the SpO2 measurement with conventional two channel measurement and Curve K5 shows the SpO2 measurement with contact reference with SpO2 variation in a static subject. Significant signal quality degradation observed even with a static subject for the two channel measurement. C1 (=61) and C2 (=300) constants were obtained by matching the SpO2 camera trace with the reference.

Figure 8:
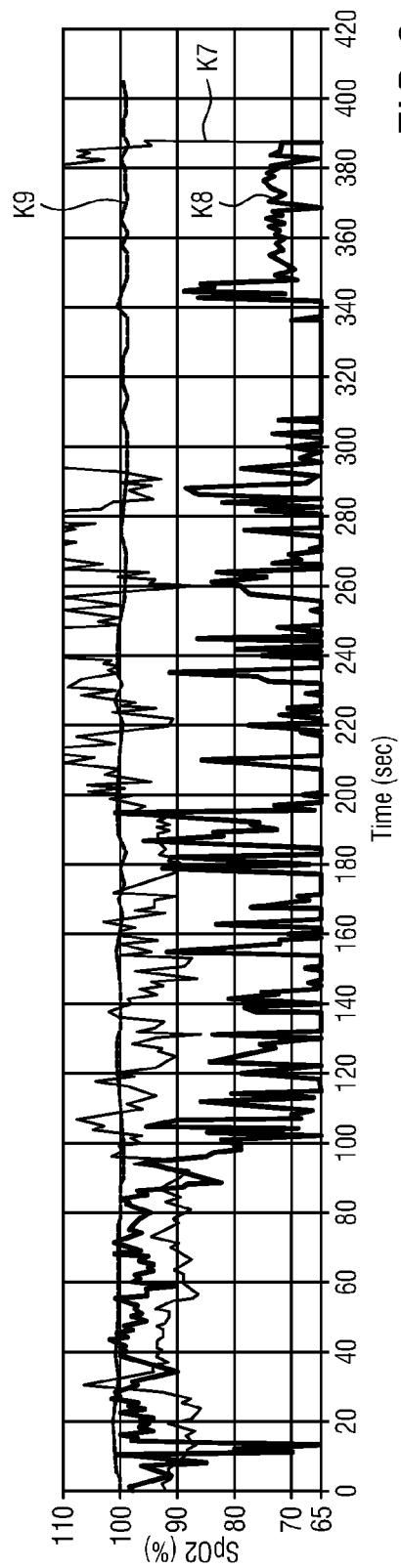
FIG. 8 shows simulation results of SpO2 measurement in a second simulation with motion of the subject.

In the second camera experiment, a subject in continuous and periodic motion is used to evaluate the performance of the algorithm. To ensure a fair comparison, the calibration constants (C1, C2) used were taken from the previous experiment. The entire recording is divided into multiple sections indicating the amount of motion added (from no motion to very high motion as time increases). FIG. 8 shows measurement results. In particular, curve K6 shows SpO2 measurement with three channel difference signals, curve K7 shows conventional two channel measurement and curve K8 shows contact reference with motion of the subject. Significant signal quality degradation can be observed even with a static subject. C1 (=61) and C2 (=300) constants were obtained by matching the SpO2 camera trace with the reference.

As can be seen from the results the result obtained using the difference measurement technique proposed in the present invention provides a much more stable version of the SpO2 signal than the conventional method. The variations still observed are assumed due to a sub-optimal setup with different optical paths for the different wavelengths used in this technique. These experiments prove that motion artifacts can be reduced significantly with the proposed invention.

Figure 9:
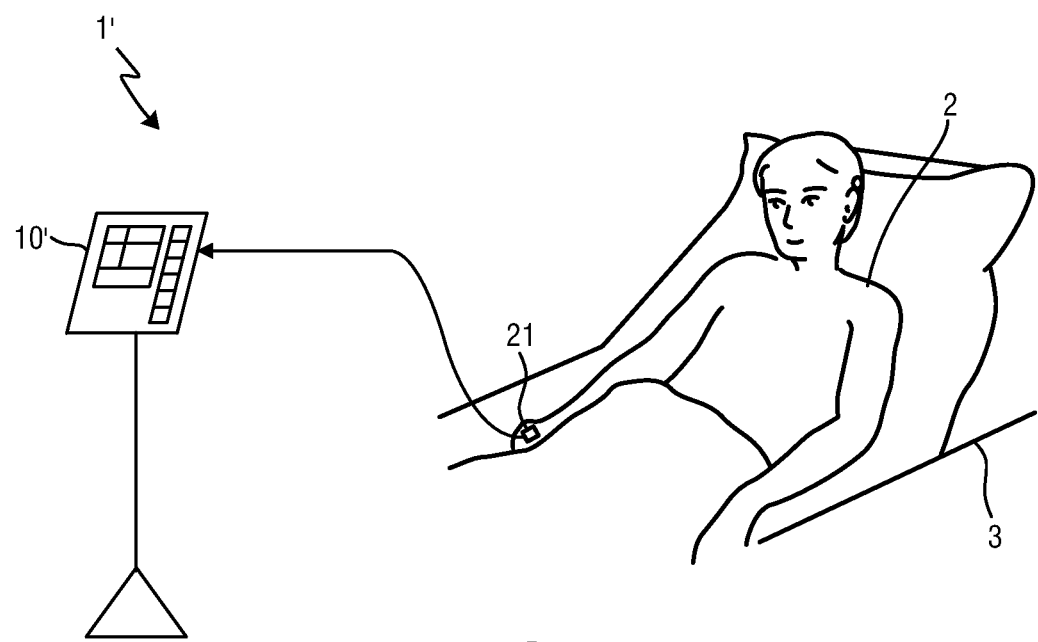
FIG. 9 shows a schematic diagram of a second embodiment of a system and device for determining the oxygen saturation of a subject.

FIG. 9 shows a schematic diagram of a second embodiment of a system 1' and device 10' for determining the oxygen saturation of a subject 2. In this embodiment instead of an imaging unit (20 in FIG. 1) a contact PPG sensor 21 is provided. Such a contact PPG sensor 21 is generally known and comprises a light unit and a photosensor. Said contact PPG sensor 21 is mounted to the body of the subject 2, e.g. to the arm, finger, nose, earlobe, etc., i.e. is configured to contact said skin area of the subject for detecting sensor signals as detection signals.

The main application of the present invention is the measurement of contactless SpO2 robust to the presence of specular reflectance and/or motion for patient monitoring applications in the NICU and general ward. The present invention is equally applicable for contact vital signs sensors and remote (camera-based) PPG systems, and can also be used to determine the concentration of other substances in the subject's blood, such as CO2 or bilirubin.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or an does not exclude a plurality. A single element or other unit may fulfill the functions of several items recited in the claims. The mere fact that certain measures are recited in mutually different dependent claims does not indicate that a combination of these measures cannot be used to advantage.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

The invention claimed is:

1. A device for determining the concentration of a substance in the blood of a subject, comprising:
at least one processor programmed to:
receive detection signals reflected back or transmitted through a skin area of the subject in response to irradiation of the skin area by a radiation signal,
extract at least three photo-plethysmography, PPG, signals at different wavelengths from said detection signals,
direct current (DC) normalize said at least three PPG signals and to form a first difference signal between a first normalized PPG signal and a second normalized PPG signal and a second difference signal between a third normalized PPG signal and one other of the at least three normalized PPG signals and to form a ratio between estimated alternating current (AC) amplitudes of said first difference signal and said second difference signal, and
calculate the concentration of a substance in the blood of the subject based on said ratio.

2. The device as claimed in claim 1, wherein the at least one processor is further programmed to:
extract two PPG signals at two wavelengths of infrared light the first and third PPG signals and one wavelength of visible or infrared light from said detection signals.

3. The device as claimed in claim 2,
wherein the two PPG signals at two wavelengths of infrared light represent the first and third PPG signals and the PPG signal at the wavelength of visible or infrared light represents the second PPG signal.

4. The device as claimed in claim 3, wherein the at least one processor is further programmed to:
form the first difference signal by subtracting the second normalized PPG signal from the first normalized PPG signal,
form the second difference signal by subtracting the first normalized PPG signal from the third normalized PPG signal; and
form said ratio by dividing said first difference signal by said second difference signal.

5. The device as claimed in claim 4, wherein the at least one processor is further programmed to:
calculate the concentration of the substance by multiplying said ratio with a second calibration parameter and subtracting the result of said multiplication from a first calibration parameter or to determine the concentration of the substance by use of a look-up table.

6. The device as claimed in claim 1, wherein the at least one processor is further programmed to:
extract a first PPG signal at a first wavelength in the range from 780 nm to 850 nm, a second PPG signal at a second wavelength in the range from 550 to 780 nm and a third PPG signal at a third wavelength in the range from 840 nm to 1000 nm.

7. The device as claimed in claim 1,
wherein said detection signals are sensor signals of a contact PPG sensor contacting said skin area of the subject.

8. The device as claimed in claim 1,
wherein said detection signals are images of at least said skin area of the subject obtained by a white-balanced imaging device.

9. The device as claimed in claim 1, wherein the at least one processor is further programmed to:
form the ratio between a standard deviation of said first difference signal and said second difference signal.

10. A system for determining the concentration of a substance in the blood of a subject, comprising:
a radiation detector configured to detect detection signals reflected back or transmitted through a skin area of the subject in response to irradiation of the skin area by a radiation signal, and
a device as claimed in claim 1 configured to determine the concentration of a substance in the blood of the subject from said detection signals.

11. The system as claimed in claim 10,
wherein said radiation detector comprises a contact PPG sensor configured to contact said skin area of the subject for detecting sensor signals as detection signals.

12. The system as claimed in claim 10,
wherein said radiation detector comprises an imaging unit for obtaining images of at least said skin area of the subject as detection signals.

13. The system as claimed in claim 10,
wherein said radiation detector comprises at least one processor programmed to obtain images of at least said skin area of the subject as detection signals.

14. A computer readable non-transitory medium having instructions stored thereon which, when carried out on a computer, cause the computer to perform a method for determining the concentration of a substance in the blood of a subject, the method comprising:
receiving detection signals reflected back or transmitted through a skin area of the subject in response to irradiation of the skin area by a radiation signal,
extracting at least three photo-plethysmography, PPG, signals at different wavelengths from said detection signals,
direct current (DC) normalizing said at least three PPG signals,
forming a first difference signal between a first PPG signal and a second PPG signal and a second difference signal between a third PPG signal and one other of the at least three PPG signals,
forming a ratio between estimated AC amplitudes of said first difference signal and said second difference signal, and
calculating the concentration of a substance in the blood of the subject based on said ratio.

15. A device for determining the oxygen saturation of a subject, comprising:
at least one processor programmed to:
receive detection signals reflected back or transmitted through a skin area of the subject in response to irradiation of the skin area by a radiation signal,
extract at least three photo-plethysmography, PPG, signals at different wavelengths from said detection signals,
direct current (DC) normalize said at least three PPG signals and to form a first difference signal between a first normalized PPG signal and a second normalized PPG signal and a second difference signal between a third normalized PPG signal and one other of the at least three normalized PPG signals and to form a ratio between estimated alternating current (AC) amplitudes of said first difference signal and said second difference signal, and
calculate the oxygen saturation of the subject based on said ratio.

16. The device as claimed in claim 15, wherein the at least one processor is further programmed to:
extract two PPG signals at two wavelengths of infrared light the first and third PPG signals and one wavelength of visible or infrared light from said detection signals.

17. The device as claimed in claim 16,
wherein the two PPG signals at two wavelengths of infrared light represent the first and third PPG signals and the PPG signal at the wavelength of visible or infrared light represents the second PPG signal.

18. The device as claimed in claim 17, wherein the at least one processor is further programmed to:
form the first difference signal by subtracting the second normalized PPG signal from the first normalized PPG signal,
form the second difference signal by subtracting the first normalized PPG signal from the third normalized PPG signal; and
form said ratio by dividing said first difference signal by said second difference signal.

19. The device as claimed in claim 18, wherein the at least one processor is further programmed to:
calculate the concentration of the substance by multiplying said ratio with a second calibration parameter and subtracting the result of said multiplication from a first calibration parameter or to determine the concentration of the substance by use of a look-up table.

20. The device as claimed in claim 15, wherein the at least one processor is further programmed to:
extract a first PPG signal at a first wavelength in the range from 780 nm to 850 nm, a second PPG signal at a second wavelength in the range from 550 to 780 nm and a third PPG signal at a third wavelength in the range from 840 nm to 1000 nm.

* * * * *